United States Patent
Ward

(10) Patent No.: US 8,652,128 B2
(45) Date of Patent: Feb. 18, 2014

(54) ELECTROSURGICAL SYSTEM HAVING A SENSOR FOR MONITORING SMOKE OR AEROSOLS

(75) Inventor: Arlen K. Ward, Thornton, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/443,066

(22) Filed: Apr. 10, 2012

(65) Prior Publication Data

US 2012/0197250 A1    Aug. 2, 2012

Related U.S. Application Data

(62) Division of application No. 12/189,272, filed on Aug. 11, 2008, now Pat. No. 8,172,836.

(51) Int. Cl.
*A61B 18/04* (2006.01)

(52) U.S. Cl.
USPC .......................................................... 606/38

(58) Field of Classification Search
USPC ......................................... 606/32–52; 607/115
See application file for complete search history.

(56) References Cited

U.S. PATENT DOCUMENTS

| | | | |
|---|---|---|---|
| 4,060,088 A | 11/1977 | Morrison, Jr. et al. | |
| 5,065,140 A | 11/1991 | Neuburger | |
| 5,201,215 A | 4/1993 | Granstaff et al. | |
| 5,273,524 A | 12/1993 | Fox et al. | |
| 5,554,172 A * | 9/1996 | Horner et al. | 607/88 |
| 5,575,789 A | 11/1996 | Bell et al. | |
| 5,613,966 A | 3/1997 | Makower et al. | |
| 6,111,512 A | 8/2000 | Sugimoto et al. | |
| 6,146,353 A | 11/2000 | Platt, Jr. | |
| 6,190,383 B1 | 2/2001 | Schmaltz et al. | |
| 6,524,307 B1 | 2/2003 | Palmerton et al. | |
| 6,658,915 B2 | 12/2003 | Sunshine et al. | |
| 6,837,095 B2 | 1/2005 | Sunshine et al. | |
| 7,197,911 B1 | 4/2007 | Lilienfeld | |
| 7,241,294 B2 | 7/2007 | Reschke | |
| D574,323 S | 8/2008 | Waaler | |
| 7,477,993 B2 | 1/2009 | Sunshine et al. | |
| 2002/0158767 A1 * | 10/2002 | Nishikawa et al. | 340/577 |
| 2004/0135684 A1 | 7/2004 | Steinthal et al. | |
| 2006/0179918 A1 | 8/2006 | Liu | |
| 2006/0191319 A1 | 8/2006 | Kurup | |
| 2007/0135812 A1 | 6/2007 | Sartor | |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

U.S. Appl. No. 10/406,690, filed Apr. 3, 2003, Robert J. Behnke, II.

(Continued)

*Primary Examiner* — Matthew F DeSanto

(57) ABSTRACT

An electrosurgical system includes an electrosurgical generator configured to generate electrosurgical energy and a sensor. The sensor is coupled to the electrosurgical generator and senses aerosol and/or smoke generated during application of the electrosurgical energy. The sensor generates data in response to the sensed aerosol and/or smoke and communicates the data to the electrosurgical generator. The electrosurgical generator generates the electrosurgical energy as a function of the data.

6 Claims, 5 Drawing Sheets

(56) References Cited

U.S. PATENT DOCUMENTS

| | | | |
|---|---|---|---|
| 2007/0203448 | A1* | 8/2007 | Melker et al. ............ 604/24 |
| 2008/0184801 | A1 | 8/2008 | Lee et al. |
| 2011/0022353 | A1 | 1/2011 | Wudy et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1776929 | 4/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |
| WO | WO2008/053532 | 5/2008 |

OTHER PUBLICATIONS

U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/566,173, filed Sep. 24, 2009, James A. Gilbert.
U.S. Appl. No. 12/566,233, filed Sep. 24, 2009, William N. Gregg.
U.S. Appl. No. 12/567,966, filed Sep. 28, 2009, Craig A. Keller.
U.S. Appl. No. 12/613,876, filed Nov. 6, 2009, Craig A. Keller.
U.S. Appl. No. 12/619,234, filed Nov. 16, 2009, James A. Gilbert.
U.S. Appl. No. 12/639,210, filed Dec. 16, 2009, Jennifer S. Harper.
U.S. Appl. No. 12/712,712, filed Feb. 25, 2010, Mani N. Prakash.
U.S. Appl. No. 12/713,956, filed Feb. 26, 2010, Robert B. Smith.
U.S. Appl. No. 12/715,212, filed Mar. 1, 2010, Robert J. Behnke, II.
U.S. Appl. No. 12/793,136, filed Jun. 3, 2010, Gary M. Couture.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 12, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487.
Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.

(56) References Cited

OTHER PUBLICATIONS

Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10191319.2 dated Feb. 22, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
Weld et al., "Analysis of Surgical Smoke Produced by Various Energy-Based Instruments and Effect on Laparoscopic Visibility", Journ. of Endourology, vol. 21, No. 3 (Mar. 2007).

* cited by examiner

ELECTROSURGICAL SYSTEM HAVING A SENSOR FOR MONITORING SMOKE OR AEROSOLS

CROSS-REFERENCE TO RELATED APPLICATIONS

This application is a divisional of U.S. patent application Ser. No. 12/189,272, filed Aug. 11, 2008 and entitled "Electrosurgical System Having a Sensor for Monitoring Smoke or Aerosols," the contents of which are hereby incorporated by reference herein in their entirety.

BACKGROUND

1. Technical Field

The present disclosure relates generally to an electrosurgical system for treating tissue. More particularly, the present disclosure is directed to an electrosurgical system having a sensor for monitoring smoke or aerosols.

2. Background of Related Art

Electrosurgery involves the application of electricity and/or electromagnetic energy to cut, dissect, ablate, coagulate, seal tissue, or other wise treat biological tissue during a surgical procedure. Additionally, certain electrosurgical modes invoke the application of electric spark to biological tissue, for example, human flesh or the tissue of internal organs, without significant cutting. The spark is produced by bursts of radio-frequency electrical energy generated from an appropriate electrosurgical generator. Generally, fulguration is used to coagulate, cut or blend body tissue. Coagulation is defined as a process of desiccating tissue wherein the tissue cells are ruptured and dehydrated/dried. Electrosurgical cutting, on the other hand, includes applying an electrical spark to tissue in order to produce a cutting or dividing effect. Blending includes the function of cutting combined with the production of a hemostasis effect.

Generally, electrosurgery utilizes an energy generator, an active electrode and a return electrode. The energy generator generates an electromagnetic wave (referred to herein as "electrosurgical energy"), typically above 100 kilohertz to avoid muscle and/or nerve stimulation between the active and return electrodes when applied to tissue. During electrosurgery, current generated by the electrosurgical generator is conducted through the patient's tissue disposed between the two electrodes. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The current causes the tissue to heat up as the electromagnetic wave overcomes the tissue's impedance. Although many other variables affect the total heating of the tissue, usually more current density directly correlates to increased heating.

Electrosurgical instruments have become widely used by surgeons in recent years. Accordingly, a need has developed for equipment and instruments, which are easy to handle, and are reliable and safe in an operating environment. Most electrosurgical instruments are hand-held instruments, e.g., an electrosurgical pencil, which transfer electrosurgical energy to a tissue site. During surgery, these electrosurgical instruments generally produce an aerosol or plume (typically referred to as "smoke" by surgeons) when organic material (e.g., the tissue of the patient) is being vaporized. The aerosol created by the vaporization of the organic material is offensive and possibly hazardous when inhaled. The aerosol may include gases such as carbon monoxide as well as solids or liquids suspended in the gas. In addition, the aerosol may include virions, which may be infectious.

The aerosol or smoke may be aspirated by a conventional suction tube held near the site of the electrosurgical procedure by an assistant. Unfortunately, this method can be inefficient since it requires the full time attention of the assistant. In addition, the placement of the often-bulky suction tube in the operative field of the surgeon may obstruct the surgeon's view. These suction tubes also typically operate on a continuous basis and create substantial noise levels during surgery thus potentially interfering with normal operating room dialogue.

Accordingly, electrosurgical instruments sometimes include integrated systems for aspirating the plume produced by the electrosurgical instruments during the electrosurgical procedures as well as for aspirating excess blood of bodily fluids prior to coagulating the remaining vessels have been developed. Electrosurgical instruments have been developed which include an aspirating system including a suction tube having at least one suction opening disposed in close proximity to the active electrode and a proximal end, which is in fluid communication with a remote source of vacuum, such as a fluid pump.

SUMMARY

The present disclosure relates generally to an electrosurgical system that can treat tissue. More particularly, the present disclosure is directed to an electrosurgical system having a sensor for monitoring smoke or aerosols.

In one embodiment of the present disclosure, an electrosurgical system includes an electrosurgical generator configured to generate electrosurgical energy and a sensor. The sensor is coupled to the electrosurgical generator to sense aerosol and/or smoke generated during application of the electrosurgical energy. The sensor generates data in response to the sensed aerosol and/or smoke and communicates the data to the electrosurgical generator. The electrosurgical generator generates the electrosurgical energy as a function of the data. The electrosurgical system also includes an electrosurgical instrument operatively coupled to the electrosurgical generator to receive the electrosurgical energy therefrom. The sensor is disposed in spaced relation to the electrosurgical instrument.

In one embodiment, the sensor includes a quartz crystal microbalance. The electrosurgical generator determines a resonance frequency of the quartz crystal microbalance utilizing the data. The electrosurgical generator also includes a sensor component operatively coupled to the quartz crystal microbalance to receive the data therefrom. The sensor component is adapted to drive the quartz crystal microbalance with a drive current. In one embodiment, the sensor component may drive the quartz crystal microbalance with at least one pulse of the drive current to determine a dissipation of the quartz crystal microbalance.

In another embodiment of the present disclosure, the sensor senses gas suspended particulates in the aerosol and estimates a generation rate of the generated aerosol and/or generated smoke. The electrosurgical generator generates the electrosurgical energy such that a generation rate of the generated aerosol and/or the generated smoke is below a predetermined threshold. The electrosurgical generator may be configured to generate electrosurgical energy such that the generation rate is below a predetermined threshold and/or is within a predetermined range. Additionally or alternatively, the electrosurgical generator may generate electrosurgical energy such that the generation rate of the generated smoke is about zero. The predetermined range may be a function of a predetermined tissue effect, e.g., hemostasis. The predetermined tissue effect may be settable, or automatically derived via an algorithm or look-up table.

In another embodiment of the present disclosure, the system includes an evacuator apparatus that evacuates the aerosol and/or smoke generated during application of the electrosurgical energy along a fluid path. The fluid path includes the vicinity of the electrosurgical instrument, inside a hose, inside a pump, within a filter and the vicinity of the portion of the evacuator apparatus that ejects filtered air. The sensor may be disposed along the fluid path and monitors the aerosol and/or smoke.

In another embodiment of the present disclosure, a method of treating tissue is disclosed includes the steps of: providing an electrosurgical generator configured to generate electrosurgical energy; and providing an electrosurgical instrument operatively coupled to the electrosurgical generator for receiving the electrosurgical energy therefrom. The method also includes the steps of: generating the electrosurgical energy; and monitoring the electrosurgical instrument for at least one of aerosol and smoke generated during application of the electrosurgical energy. The method also includes the steps of generating data in response to the sensed aerosol and/or smoke and communicating the data of the monitored aerosol and/or the smoke to the electrosurgical generator. The method also includes the step of adjusting the electrosurgical energy as a function of the data.

In another embodiment of the present disclosure, the monitoring step may include utilizing a quartz crystal microbalance and the method may include the step of determining a resonance frequency of the quartz crystal microbalance. The step of adjusting may adjust the electrosurgical energy such that a generation rate of the generated aerosol and the generated smoke is below a predetermined threshold, the generated smoke is about zero, or the generation rate is within a predetermined range.

In another embodiment of the present disclosure, an electrosurgical instrument includes one or more electrodes and a sensor. The one or more electrodes apply electrosurgical energy to tissue. The sensor is disposed on the electrosurgical instrument and senses aerosol and/or smoke generated during the application of the electrosurgical energy. The sensor generates data in response to the sensed aerosol and/or smoke.

BRIEF DESCRIPTION OF THE DRAWINGS

Various embodiments are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
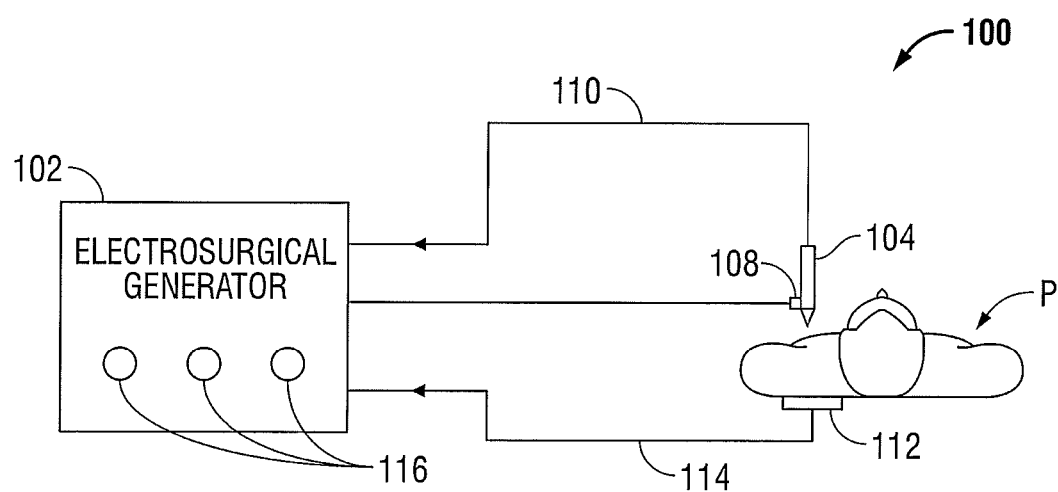
FIG. 1 is a schematic diagram of an electrosurgical system having a smoke and aerosol sensing system in accordance with the present disclosure.

Referring to the drawings, FIG. 1 illustrates an electrosurgical system 100 according to an embodiment of the present disclosure. Electrosurgical system 100 includes an electrosurgical generator 102 coupled to an electrosurgical instrument 104. Electrosurgical instrument 104 includes a sensor 108 adapted to monitor electrosurgical instrument 104. Sensor 108 senses aerosols and/or smoke generated during application of electrosurgical energy. Sensor 108 is coupled to electrosurgical generator 102 and communicates data thereto. Electrosurgical generator 102 applies the electrosurgical energy as a function of the data from sensor 108 as discussed in more detail below.

Electrosurgical instrument 104 has one or more active electrodes for treating tissue of patient P. Electrosurgical instrument 104 maybe any type of electrosurgical instrument (e.g., monopolar or bipolar) and may include active electrodes designed for a wide variety of electrosurgical procedures (e.g., electrosurgical cutting, ablation, etc.). Electrosurgical energy is supplied to electrosurgical instrument 104 by electrosurgical generator 102 via cable 110, which is connected to an active output terminal, allowing electrosurgical instrument 104 to coagulate, ablate, and/or otherwise treat tissue by causing hemostasis. The electrosurgical energy is returned to electrosurgical generator 102 through return pad 112 via cable 114 after passing through patient P.

The electrosurgical generator 102 includes input controls 116 (e.g., buttons, activators, switches, touch screen, etc.) for controlling electrosurgical system 100. In addition, electrosurgical generator 102 includes one or more display screens (not explicitly shown) for providing the user with variety of output information (e.g., intensity settings, treatment complete indicators, etc.). The controls 116 allow the user (e.g., a surgeon, nurse, or technician) to adjust the electrosurgical energy parameters (e.g., power, waveform, duty cycle, voltage, current, frequency, and/or other parameters) to achieve the desired electrosurgical energy characteristics suitable for a particular task (e.g., coagulating, tissue sealing, intensity setting, etc.). Additionally or alternatively, input controls 116 may include a settable desired tissue effect (e.g., hemostasis, coagulation, ablation, dissection, cutting, and/or to sealing tissue). The electrosurgical instrument 104 may also include one or more input controls (not explicitly shown) that may be redundant with input controls 116 of electrosurgical generator 102. Placing the input controls on the electrosurgical instrument 104 allows for easier and faster modification of the electrosurgical energy during the surgical procedure without requiring interaction with electrosurgical generator 102.

Figure 2:
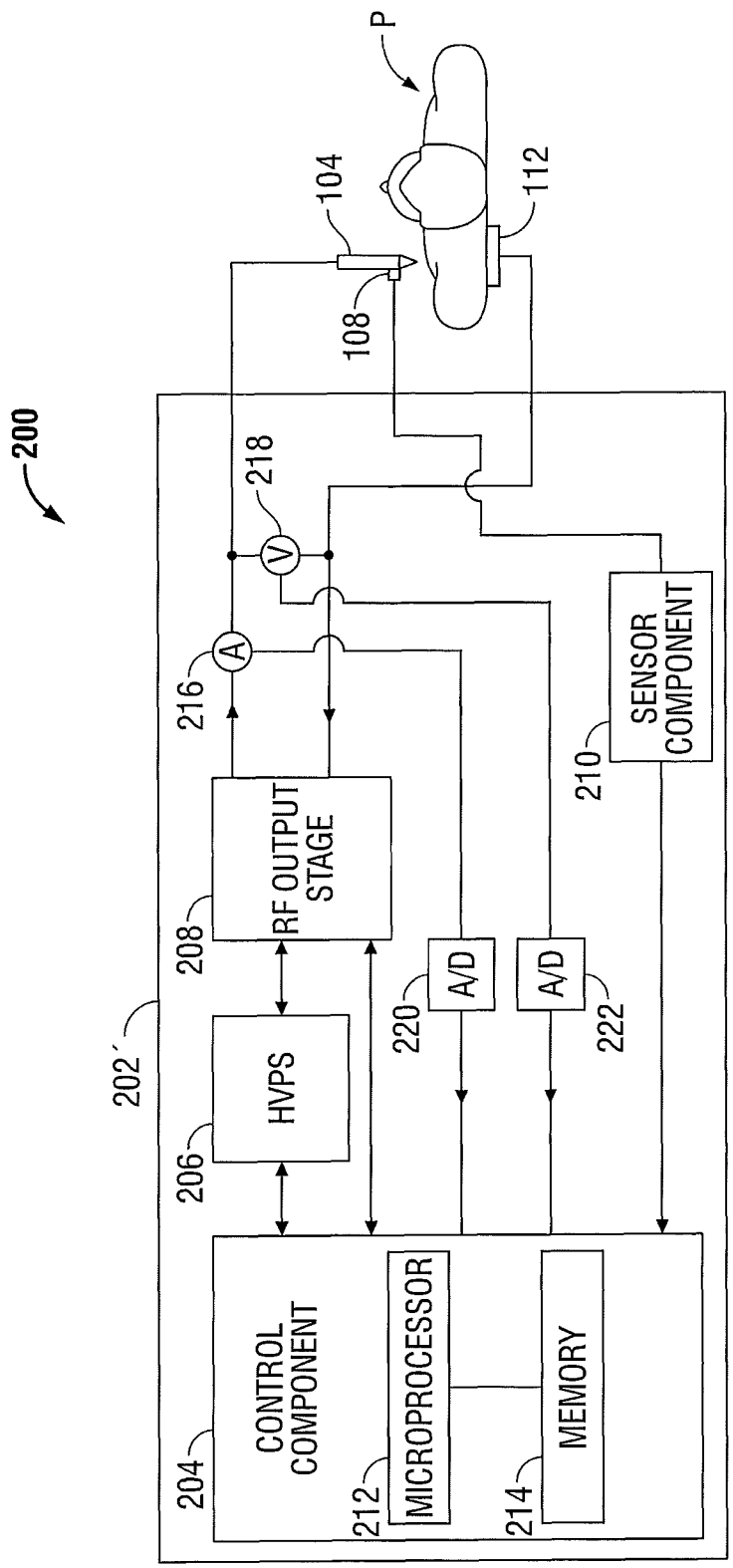
FIG. 2 is a schematic diagram of an electrosurgical generator coupled to a smoke and aerosol sensor in accordance with the present disclosure.

Referring to the drawings, FIG. 2 shows a schematic block diagram of an electrosurgical system 200 including an electrosurgical generator 202 in accordance with the present disclosure. Electrosurgical generator 202 includes a control component 204, a high voltage DC power supply 206 ("HVPS"), an RF output stage 208, and a sensor component 210. HVPS 206 provides high voltage DC power to RF output stage 208, which then converts high voltage DC power into electrosurgical energy and delivers the electrosurgical energy to electrosurgical instrument 104. In particular, RF output stage 208 generates sinusoidal waveforms of electrosurgical energy. RF output stage 208 can generate a plurality of waveforms having various duty cycles, peak voltages, crest factors and other suitable parameters. Certain types of waveforms are suitable for specific electrosurgical modes. For instance, RF output stage 208 generates a 100% duty cycle sinusoidal waveform in cut mode, which is best suited for ablating, fusing and dissecting tissue, and a 1-25% duty cycle waveform in coagulation mode, which is best used for cauterizing tissue to stop bleeding.

Control component 204 includes a microprocessor 212 operably connected to a memory 214, which may be volatile type memory (e.g., RAM) and/or non-volatile type memory (e.g., flash media, disk media, etc.). Control component 204 includes an output port that is operably connected to the HVPS 306 and/or RF output stage 208 that allows the control component 204 to control the output of electrosurgical generator 202 according to either open and/or closed control loop schemes. Control component 202 may include any suitable logic processor (e.g., control circuit), hardware, software, firmware, or any other logic control adapted to perform the features discussed herein.

Electrosurgical generator 202 includes a current sensor 216 and a voltage sensor 218, and also includes an interface into sensor 108 (and may include other sensors) for measuring a variety of tissue and energy properties (e.g., tissue impedance, output current and/or voltage, etc.) and to provide feedback to the control component 204 based on the measured properties. Current sensor 216 and voltage sensor 218 interface into control component 204 via A/D converters 220 and 222, respectively. Such sensors are within the purview of those skilled in the art. Control component 204 sends signals to HVPS 206 and/or RF output stage 208 to control the DC and/or RF power supplies, respectively. Control component 204 also receives input signals from the input controls (not shown) of the electrosurgical generator 202 or electrosurgical instrument 104. Control component 304 utilizes the input signals to adjust the output power or the electrosurgical waveform of the electrosurgical generator 202 and/or perform other control functions therein. For example, control component 204 may utilize a feedback loop control algorithm such as a P-I-D control algorithm Sensor 108 senses aerosol and/or smoke generated during application of electrosurgical energy to tissue and communicates data related to the sensed aerosol and/or smoke to electrosurgical generator 102. The aerosol or smoke generated during electrosurgery may include gases, water vapor, suspended particulates, suspended particles and liquids.

Electrosurgical generator includes sensor component 210 that interfaces into sensor 108. As previously mentioned, sensor 108 includes a QCM. Sensor component 210 utilizes the QCM to communicate aerosol or smoke data to control component 204. Control component 204 controls the generation of the electrosurgical energy as a function of the data. For example, control component 204 may adjust the electrosurgical energy to achieve energy-deposited values 410 and 412, or energy deposited range 416 (discussed below).

Sensor component 210 may be implemented in suitable circuitry, hardware, software, firmware, bytecode or some combination thereof Sensor component 210 includes an AC source (not shown) to induce oscillations in the QCM to generate a standing shear wave. Sensor component 210 also includes a frequency sensor (not shown) and measuring circuitry (not shown). The AC source induces oscillations in the QCM while the frequency sensor determines the frequency of the induced oscillation to a sufficient accuracy. The measuring circuitry determines the "peak" frequency to determine the resonance frequency of the QCM in sensor 108. Since the frequency oscillation of the QCM is partially dependent on the deposited mass, using Equation 1 below (discussed below) the mass deposition rate can be measured and correlated to an aerosol or smoke generation rate. The resonance frequency is roughly inversely proportional to the deposited mass on the sensing surface of the QCM. However, other techniques of measuring deposited mass on the sensing surface of the QCM are within the purview of those skilled in the art and may be implemented by sensor component 210, e.g., sensor component 210 may measure impedance, "ringdown", bandwidth, Q-factor, dissipation, complex resonance, mechanical impedance and the like of the QCM. For example, the dissipation and resonance frequency of the QCM may be determined by sensor component 210 to sense the aerosol and/or smoke generated by applying a pulse to monitor the "ring-down". Sensor component 210 extracts information from the "ring-down" to determine the dissipation of the QCM. Additionally or alternatively, temperature, pressure, and/or bending stress compensation may be utilized by sensor 108.

Sensor component 210 communicates data to control component 204. The communication may be continuous or intermittent. The data may be communicated in analog form, digital form, using a pulse width modulated signal, using a frequency or analog modulated signal, or any other communication technology. Control component 204 uses the data to control the generation of the electrosurgical energy (as discussed above). Control component 204 may use the data from sensor component 210 to form a feedback control loop such as a P-I-D control algorithm. Additionally or alternatively, control component 204 may control the generation of the electrosurgical energy by apply a feed-forward control technique.

Figure 3:
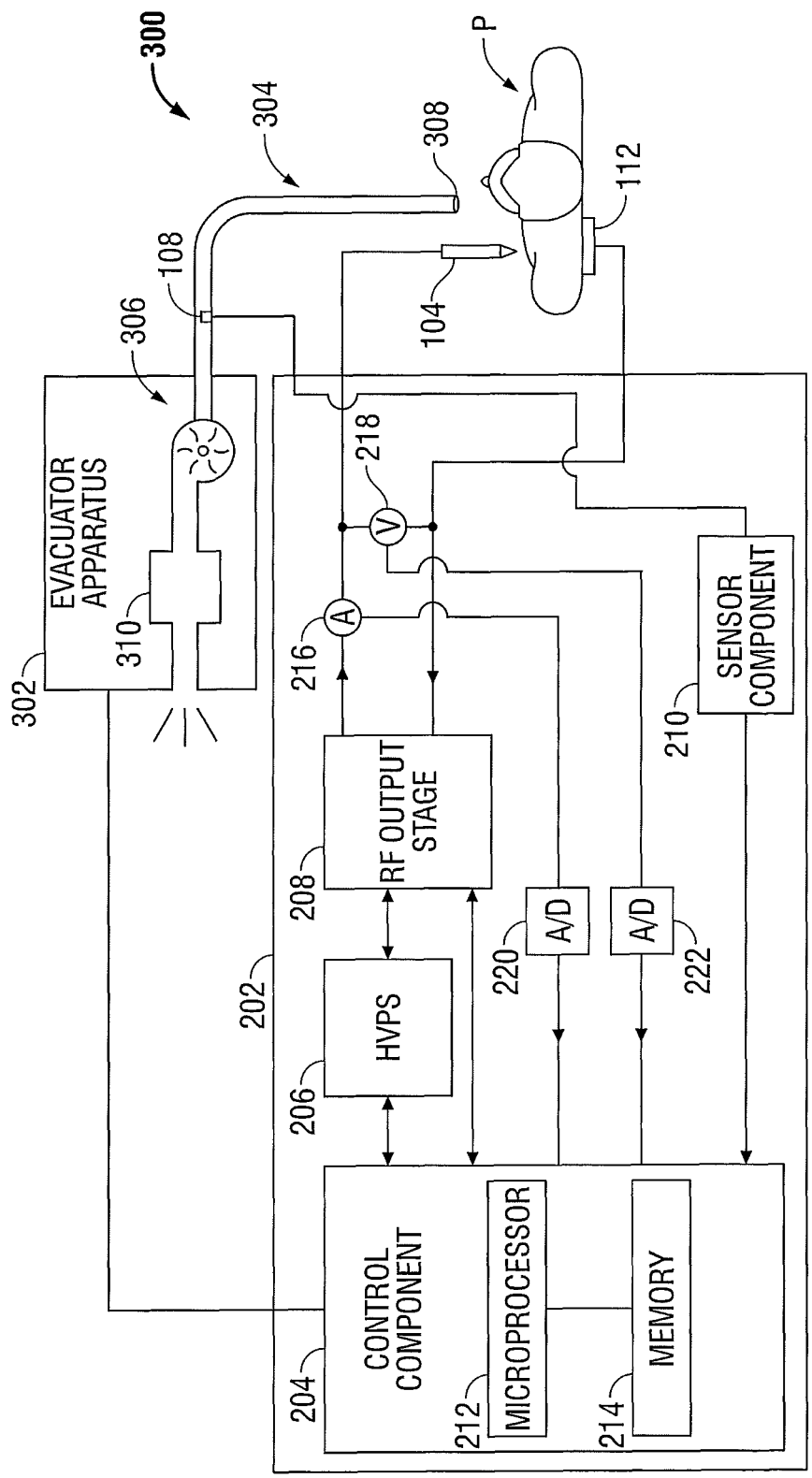
FIG. 3 is a plot showing a relationship between energy deposited relative to hemostasis and relative smoke produced in accordance with the present disclosure.

Referring to the drawings, FIG. 3 is a block diagram of an electrosurgical system 300 having an evacuator apparatus 302. The electrosurgical generator 202' is coupled to a sensor 108' disposed along a fluid path of evacuator apparatus 302 to monitor electrosurgical instrument by sensing aerosol and/or smoke in accordance with the present disclosure. Evacuator apparatus 302 includes hose 304 connected to pump 306. Air with aerosol or smoke generated during application of electrosurgery via electrosurgical instrument 104' is carried from nozzle 308 along hose 304 to pump 306. Pump 306 forces the air and smoke and/or aerosol through filter 310 to remove the aerosol or smoke from the air.

Sensor 108' is coupled to sensor component 210, which communicates data to data to control component 204. Control component 204 controls the generation of the electrosurgical energy as a function of the data from sensor 108', similarly to electrosurgical generator 102 of FIG. 1 or electrosurgical generator 202 of FIG. 2. Sensor 108' may be disposed along any portion of the fluid path. The fluid path evacuates fluid from the vicinity of electrosurgical instrument 104', within hose 304, through pump 306 and to filter 310. The fluid path includes the region around electrosurgical instrument 104', within hose 304, through pump 306, through filter 310 and the region where the filter air is ejected.

Evacuator 302 is operatively connected to control component 204. Control component 204 controls the operation of the pump 206 within evacuator apparatus 302 as a function of the aerosol or smoke sensed by sensor 108'. Additionally or alternatively, another quartz crystal microbalance may be connected to evacuator apparatus 302 to control pump 306 either directly or through electrosurgical generator 202'.

Sensor 108' may include a quartz crystal microbalance (referred to herein as "QCM") which includes a sensing surface (not explicitly shown). Sensor 108' has a resonance frequency that is related to the mass deposited or affixed to the sensing surface. The relationship between resonance frequency and mass, allows for estimation of deposited mass and/or changes in the deposited mass by monitoring the resonance frequency (or other properties) of sensor 108'. The generated aerosol or smoke deposits solid particles, particulates, liquids and/or vapors on the sensing surface of sensor 108', which changes the mass of the sensor 108' thereby affecting the resonance frequency. By monitoring the resonance frequency (or changes in the resonance frequency) of sensor 108', the aggregate (or a rate of) deposition of mass on sensor 108''s sensing surface may be used by electrosurgical generator 202' to control the generation of the electrosurgical energy based on the sensed aerosol or smoke.

The resonance frequency of sensor 108' (or sensor 108 of FIGS. 1 and 2) may be determined based on the piezoelectric properties of the QCM. Mass and frequency changes are correlated based on the Sauerbrey Equation, which assumes the mass deposited on the sensing surface is a thin film extension of the quartz crystal thereby affecting the resonance frequency. The resonance frequency is roughly inversely proportional to the deposited mass on the sensing surface of the QCM; however, temperature, pressure and bending stress also may affect the resonance frequency. The Sauerbrey Equation is Equation 1 below:

$$\Delta f = -\frac{2f_Q^2}{A\rho_Q v_Q}\Delta m \quad (1)$$

In Equation 1, $f_Q$ is the resonant frequency, $\rho_Q$ is the density of the quartz crystal and $v_Q$ is the shear wave velocity in quartz. In embodiments, the crystal structure of the QCM included in sensor 108 is conducive to $f_Q$, $\rho_Q$, and $v_Q$ having predictable values facilitating calibration without complicated or expensive equipment. The QCM is sensitive enough to detect very small masses, such as from solid particles, particulates, liquids and/or vapors deposited on the sensing surface and may be utilized to quantify aerosols or smoke generated during application of the electrosurgical generator.

Figure 4:
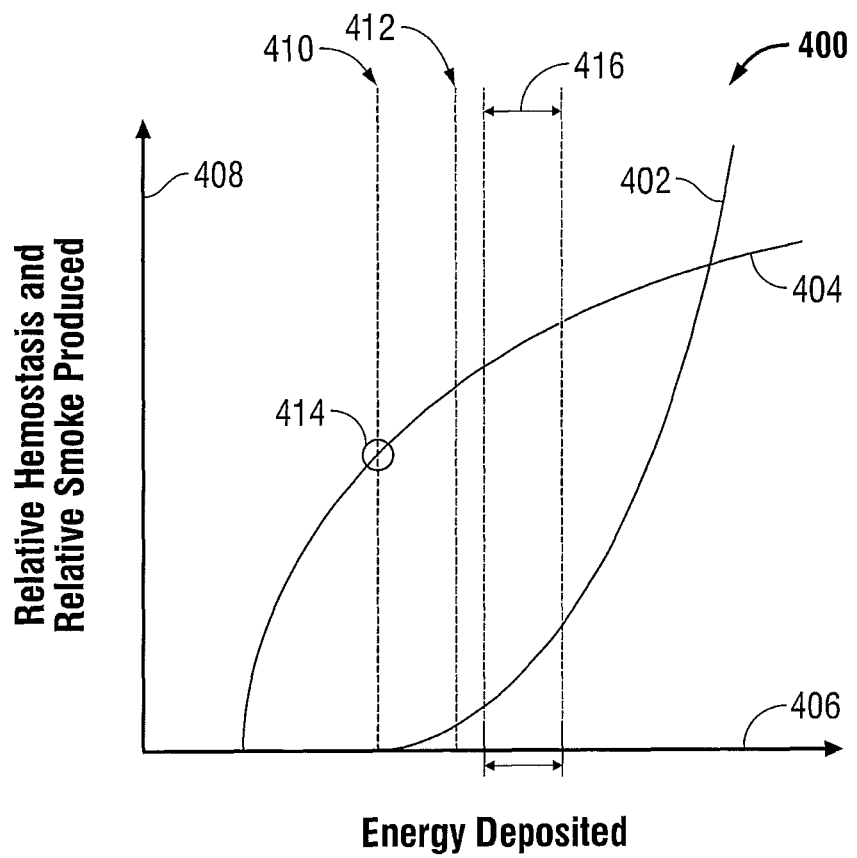
FIG. 4 is a schematic diagram of an electrosurgical generator and an evacuator apparatus in accordance with the present disclosure.

Referring to FIG. 4, a plot 400 shows a relationship between energy deposited to relative hemostasis and smoke produced in accordance with the present disclosure. Referring to FIGS. 1 and 4, plot 400 describes several control algorithms (or functions) utilized by electrosurgical generator 102 (or electrosurgical generator 202 of FIG. 2 and/or electrosurgical generator 202' of FIG. 3) to control the generation of electrosurgical energy, during which the electrosurgical generator 102 generates the electrosurgical energy as a function of sensed aerosol or smoke as monitored by sensor 108. Plot 400 includes lines 402 and 404 plotted on axes 406 and 408. Axis 406 illustrates the energy deposited onto tissue of patient P by electrosurgical generator 102. Axis 408 shows the relative hemostasis and relative smoke produced as a function of the energy deposited. Line 402 shows the smoke production rate as a function of energy deposited. First energy-deposited value 410 is a value along axis 406 of which smoke begins to generate, in other words, below first energy-deposited value 410, the generated smoke is about zero. Additionally, first energy-deposited value 410 intersects line 404 at point 414 corresponding to a value of hemostasis occurring in the tissue of patient P being treated by electrosurgical instrument 104. Thus, by applying energy at the first energy-deposited value 410, smoke is not produced and a clinically significant amount of hemostasis (see point 414) occurs in the treated tissue.

As previously mentioned, electrosurgical generator 102 has inputs 116 in which a desired tissue affect is settable. When a hemostasis tissue effect is set via input controls 116, electrosurgical generator 102 generates electrosurgical energy below energy-deposited value 410 by monitoring the smoke generation rate as sensed by sensor 108. Electrosurgical generator 102 accomplishes the desired energy-deposited value 410 by reducing the electrosurgical energy such that the sensed generation rate of smoke is below a predetermined threshold. Electrosurgical generator may generate the electrosurgical energy such that the smoke generation rate 402 is about zero (in hemostasis mode) while the hemostasis rate is sufficient to treat tissue In certain situations, it may be desirable to supply additional energy at the expense of smoke generated. Thus, electrosurgical generator 102 in another embodiment adjusts the electrosurgical energy based on a second energy-deposited value 412, in which a minimal amount of smoke is generated. Second energy-deposited value 412 is accomplished by electrosurgical generator 102 controlling the generation of the electrosurgical energy to remain below another predetermined threshold. Other ranges or value may be utilized by electrosurgical generator 102, e.g., electrosurgical generator 102 may control the generation of the electrosurgical energy to achieve energy-deposited range 416.

Figure 5:
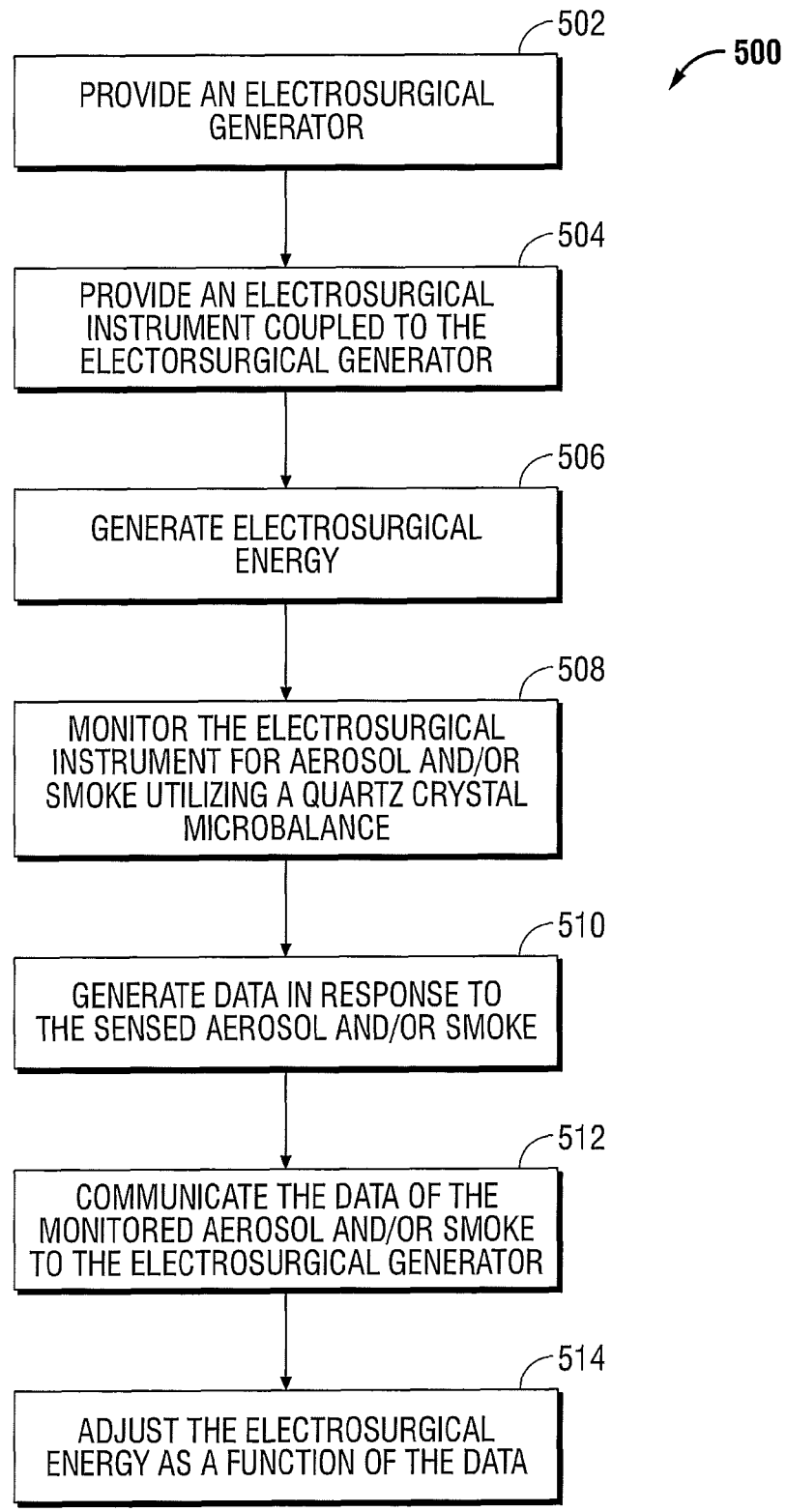
FIG. 5 is a flow chart diagram of a method of treating tissue by monitoring an electrosurgical instrument for aerosol and/or smoke generated during application of electrosurgical energy in accordance with the present disclosure.

Referring to the drawings, FIG. 5 is a flow chart diagram of a method 500 of treating tissue in accordance with the present disclosure. Method 500 includes steps 502 through 512. Step 502 provides an electrosurgical generator, such as electrosurgical generator 102 of FIG. 1 or electrosurgical generator 202 of FIG. 2. Step 504 provides an electrosurgical instrument coupled to the electrosurgical generator of step 502. The electrosurgical instrument receives electrosurgical energy from the electrosurgical generator. Step 506 generates the electrosurgical energy and step 508 monitors the electrosurgical instrument for aerosol and/or smoke utilizing a QCM. Step 510 generates data in response to the sensed aerosol and/or smoke. Step 512 communicates the data of the monitored aerosol and/or smoke to the electrosurgical generator. Step 514 adjusts the electrosurgical energy as a function of the data. Step 514 may implement any of the algorithms discussed regarding FIG. 4, e.g., adjusting the electrosurgical energy such that energy-deposited value 410 is achieved.

From the foregoing and with reference to the various figure drawings, those skilled in the art will appreciate that certain modification can also be made to the present disclosure without departing from the scope of the same. For example, other aerosol, particulates or gas sensors (such as optical particle counters) may be utilized by the electrosurgical system to estimate the aerosol generation rate. Additionally, the electrosurgical instrument may be a bipolar electrosurgical instrument, e.g., such as bipolar forceps.

What is claimed is:

1. A method of treating tissue, comprising:
    continuously supplying electrosurgical energy generated by an electrosurgical generator to tissue to achieve a desired tissue effect, the continuous supplying of electrosurgical energy including:
        applying the electrosurgical energy to the tissue at a first energy value;
        sensing at least one of an aerosol and a smoke generated during application of the electrosurgical energy; and
        adjusting the supply of the electrosurgical energy to apply the electrosurgical energy to the tissue at a second energy value as a function of the sensed at least one of the aerosol and the smoke to adjust a generation rate of the at least one of the aerosol and the smoke.

2. The method according to claim 1, wherein sensing at least one of the aerosol and the smoke utilizes a quartz crystal microbalance.

3. The method according to claim 2, further comprising: determining the resonance frequency of the quartz crystal microbalance.

4. The method according to claim 1, wherein adjusting the supply of the electrosurgical energy includes applying the electrosurgical energy to the tissue at the second energy value such that the generation rate of the at least one of the aerosol and the smoke is below a predetermined threshold.

5. The method according to claim 1, wherein adjusting the supply of the electrosurgical energy includes applying the electrosurgical energy to the tissue at the second energy value such that the generation rate of the at least one of the aerosol and the smoke is about zero.

6. The method according to claim 1, wherein adjusting the supply of the electrosurgical energy includes applying the electrosurgical energy to the tissue at the second energy value such that the generation rate of the at least one of the aerosol and the smoke is within a predetermined range.

* * * * *